United States Patent [19]
Humphrey

[11] Patent Number: 4,730,910
[45] Date of Patent: Mar. 15, 1988

[54] WIDE ANGLE LENS SYSTEM HAVING FLARE REJECTION PROPERTIES

[75] Inventor: William E. Humphrey, Oakland, Calif.

[73] Assignee: Humphrey Instruments, Inc., San Leandro, Calif.

[21] Appl. No.: 777,371

[22] Filed: Sep. 18, 1985

[51] Int. Cl.$^4$ .................. G02B 13/18; G02B 9/34; G02B 27/00
[52] U.S. Cl. ................................. 350/436; 350/571
[58] Field of Search ............... 350/436, 409, 620, 571

[56] References Cited

U.S. PATENT DOCUMENTS

| | | | |
|---|---|---|---|
| 2,358,092 | 9/1944 | Luboshez | 350/409 |
| 2,979,997 | 4/1961 | Bertsch | 350/436 |
| 3,985,422 | 10/1976 | Mecklenborg et al. | 350/571 |

OTHER PUBLICATIONS

Gelles, "Unobscured Aperture Stigmatic Telescopes", Optical Engineering; Nov.–Dec. 1974; vol. 13–No. 6; pp. 534–538.

*Primary Examiner*—John K. Corbin
*Assistant Examiner*—Rebecca D. Gass
*Attorney, Agent, or Firm*—Townsend and Townsend

[57] ABSTRACT

A wide angle lens system of at least two, and preferably four, similar powered symmetrical component lenses is disclosed; these lenses are from object to image, at least two paired concavo-convex lenses, and preferably two lenses of a concavo-convex or convexo-convex type. The first and last lenses are displaced and rotated usually by rotation about the object (taken as a defining aperture of the optical system, such as a portion of the cornea) or its conjugate, in a first direction to use lens portions between the lens center and one edge; the intermediate lens (preferably the second and third lenses) are displaced and rotated (again usually by rotation about the image conjugate formed by the first lens) in an opposite direction to use the lens portions between the other lens edge and center. Deflected rays in the lens system utilize marginal portions of the lens between the center and one edge only; neither the non-deviating portion of the spherical lenses nor the opposite side of the spherical lenses are used. The lenses are non-concentric. Consequently, the lenses can be further minimally rotated as required for optimum flare rejection.

16 Claims, 17 Drawing Figures

WIDE ANGLE LENS SYSTEM HAVING FLARE REJECTION PROPERTIES

BACKGROUND OF THE INVENTION

This invention relates to a wide angle lens system and preferably a wide angle lens system for rejecting flare.

SUMMARY OF THE PRIOR ART

Wide angle lens systems for illuminating an object along a first path and receiving back from the object an image thereof along a second and closely adjacent path are known.

Typically the lenses are normal to a principal optical axis, and therefore generate flare. Flare is either ignored and appears as a central image artifact or is imaged at light stops with resultant central image degradation by the shadow of the light spot. Consequently, such conventional lenses may not readily be moved for focus because light escapes the built-in light stops or the image degradation caused by the stops may be worsened. Where image artifact is either ignored or does exist, it is central—usually where the "object of interest" is located.

SUMMARY OF THE INVENTION

A wide angle lens system of at least two, and preferably four, similar powered symmetrical component lenses is disclosed; these lenses are from object to image, at least two paired concavo-convex lenses, and preferably two lenses of a concavo-convex or convexo-convex type. The first and last lenses are displaced and rotated usually by rotation about the object (taken as a defining aperture of the optical system, such as a portion of the cornea) or its conjugate, in a first direction to use lens portions between the lens center and one edge; the intermediate lens (preferably the second and third lenses) are displaced and rotated (again usually by rotation about the image conjugate formed by the first lens) in an opposite direction to use the lens portions between the other lens edge and center. Deflected rays in the lens system utilize marginal portions of the lens between the center and one edge only; neither the non-deviating portion of the spherical lenses nor the opposite side of the spherical lenses are used. The lenses are non-concentric. Consequently, the lenses can be further minimally rotated as required for optimum flare rejection. After optimum displacement and rotation, lens design may be minimally altered to reduce aberration, dispersion and distortion with the result that lens system balance leaves only minor uniform astigmatism. This minor uniform astigmatism is corrected with a weak cylindrical lens, preferably placed at a conjugate to the object relative to the lens system. The lens finds preferable use in a system which projects light to an object along a first path and receives light back from the object along an immediately adjacent and second path, this reception occurring without flare. There results a wide angle system that can be composed only of spherical lenses, uses all lenses non-concentrically relative to the central field axis, has the lens elements rotated and/or translated, and presents all refractive surfaces at an angle where flare is rejected. Correction for overall residual on axis cylinder effect optimizes the system. An alternate embodiment using two aspheric lenses is shown.

OTHER OBJECTS, FEATURES AND ADVANTAGES

An object of this invention is to disclose a wide angle lens having flare rejection properties utilizing at least paired similarly powered, preferably aplanatic or near aplanatic lenses. The first lens is displaced and rotated, typically by rotation about its object point (i.e. the central corneal region of the eye) in a first direction to use lens portions between the lens center and one edge only. The other lens is displaced and rotated, typically by rotation in an opposite direction about its image conjugate, to use the lens portion between the other edge and lens center. Deflected rays in the lens system utilize marginal portions of the lenses only, with paired lens segments having substantially equal powers above and below the axes.

An advantage of the disclosed lens system is that aspheric surfaces can be avoided. Minimization of spherical aberration occurs by utilizing multiple spherical elements of approximately equal power; that is, the power of the marginal lens segments extending in one direction is balanced by the power of the marginal lens segments extending in the opposite direction.

A further advantage of the disclosed lens system is that it is possible to substantially balance all aberrations, dispersions and absorptions to the extent of preserving essentially symmetrical optical performance, save and except a mild and uniform cylindrical aberration. This latter aberration is corrected by placement of a conventional cylindrical lens, preferably at a conjugate to the overall lens system focus.

Yet another advantage of this invention is that it is also possible to prevent strong on-axis color, rotated or tilted image planes and unsymmetrical astigmatism; correction can occur to acceptable tolerances.

It is important to understand how nonconventional this lens system is. Not only can aspherical surfaces be avoided, lenses are used non-concentrically. Only the marginal portion of the lenses are utilized for imaging. Flare rejection occurs either by the initial configuration of the lens surfaces or alternatively by minute rotating of the lens elements, preferably about the center of curvature of one of the optic surfaces.

A further object of this invention is to disclose an objective lens system for use in a fundus camera. The image of an aperture plane is projected to an eye. Peripheral light sources for illumination of the fundus of the eye impinge just beyond the central corneal region of the eye. Rays exit from a region of the cornea conjugate to the camera aperture. These centrally exiting rays from the iluminated fundus form an image in a camera. Light passes along immediately adjacent optical paths without producing flare, especially from the cornea.

An advantage of the lens in a fundus camera is that it is capable of being achromatically corrected for lateral and longitudinal color aberration by optics beyond the aperture plane.

A further advantage of the flare rejecting objective is that the use of conventional flare blocking spots or stops is avoided. Consequently, the objective lens system may be moved to assist focus without having flare or image degradation. The disclosed objective lens may be used for stereo imaging simultaneously through several apertures without flare. Moreover, since light stops are absent, image degradation centrally does not occur.

Consequently, the resultant images may be quantitatively enhanced, as by digital processing.

It will be understood that although the use of the objective is preferred in a slit-scanning fundus camera, the lens system here disclosed will find use in microscopes, standard fundus cameras, cameras for imaging other portions of the eye such as the cornea, and military applications as where a target is illuminated and focused with light passing in both directions through the same lens system.

A further object of this invention is to disclose a process of designing and making the disclosed lens. Utilizing first and second concavo-convex aplanats, or near aplanats, the lens system is initially ray traced with elements placed theoretically with actual overlap between their refractive surfaces. By utilizing such overlap the lens elements may be reduced in overall length; moreover, since the rays are highly convergent to the object, corresponding reduction in lens diameter occurs. Typically, the first lens element is rotated about its object point so that all active rays pass between the lens center or apex and one edge. Thereafter, the remainder of the lens system is rotated in a opposite direction so that all active rays pass between the opposite edge and the lens center. All lenses are rotated until their marginal portions are used only. Preferably the total marginal portions above the lens centers are selected to have about the same power as the total marginal portions below the lens centers. Thereafter, all lens elements are balanced to minimize aberrations, save and except, a uniform cylinder which appears at an imaging plane of the lens system. Finally, overall lens system balance occurs by the placement of a conventional weak cylinder lens at a stop position location.

An advantage of the design process is that it may be readily ray traced with conventional ray tracing programs.

Other objects, features and advantages of this invention will become more apparent after referring to the following specification and attached drawings.

BRIEF DESCRIPTION OF THE FIGURES

FIGS. 2A–2E are cartoon series indicating the process of rotating of the lens elements to produce the lens train illustrated in FIG. 1A with:

DESCRIPTION OF THE PREFERRED EMBODIMENTS

Figure 1A:
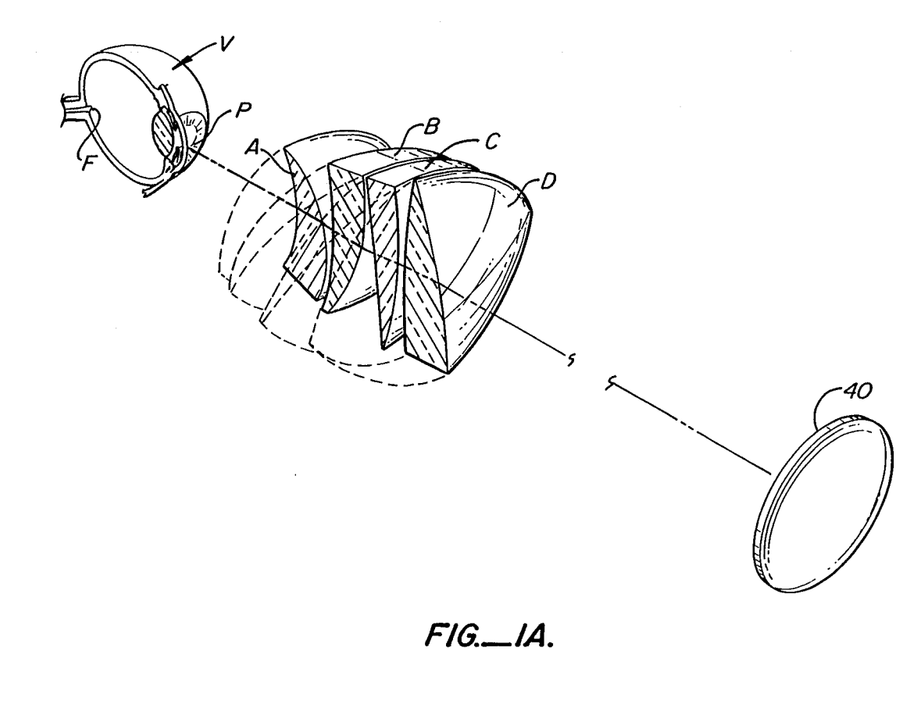
FIG. 1A is a perspective of the lens elements and correcting weak cylinder illustrating the objective lens system of this invention.

Referring to FIG. 1A, a perspective view of the lens system can be seen.

Figure 2A:
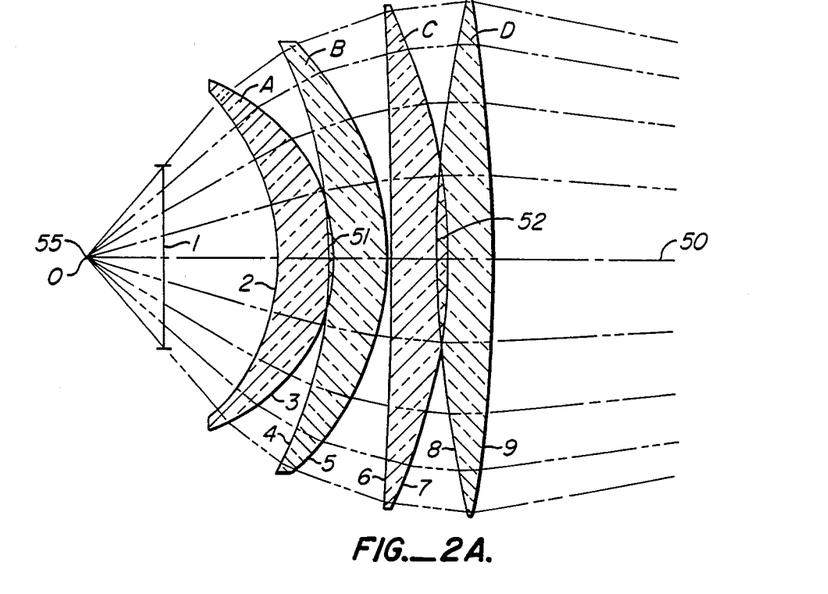
FIG. 2A being the spherical lens train from which lens design originates, the lenses are here shown concentrically aligned and overlapped.
Figure 2B:
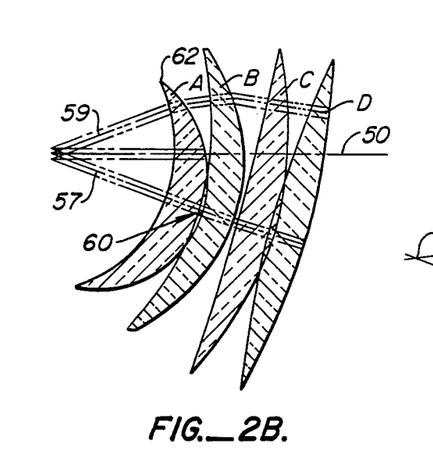
FIG. 2B showing rotation of the first lens
Figure 2C:
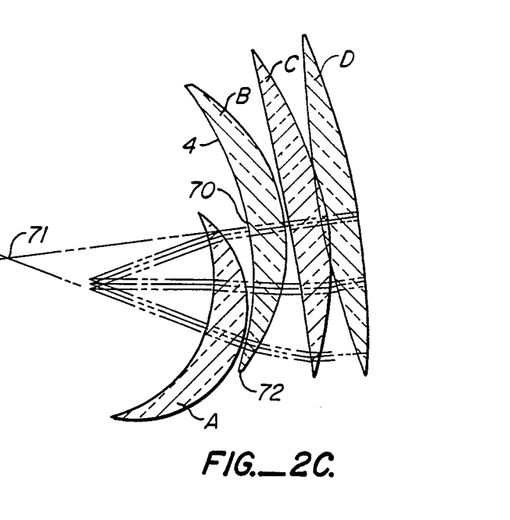
FIG. 2C showing rotation of the second, third and fourth lens elements relative to the first lens element to free overlap.
Figure 2D:
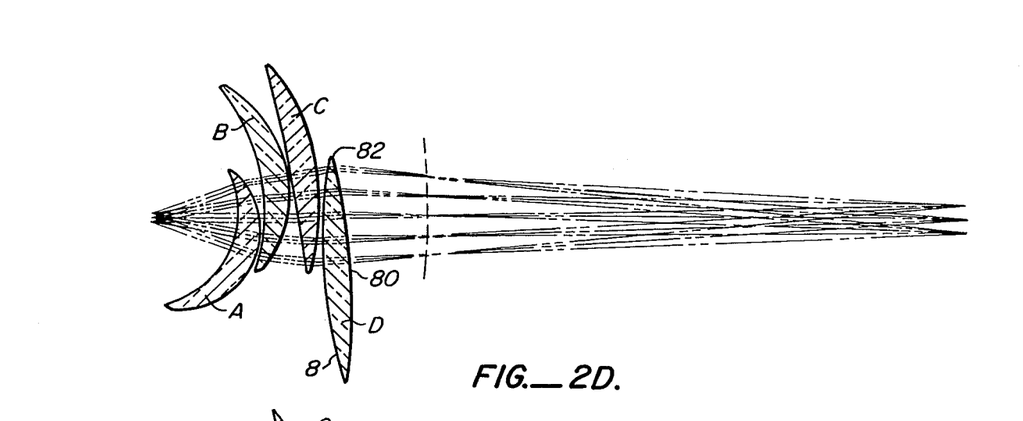
FIG. 2D showing rotation of the fourth lens element free of overlap.
Figure 2E:
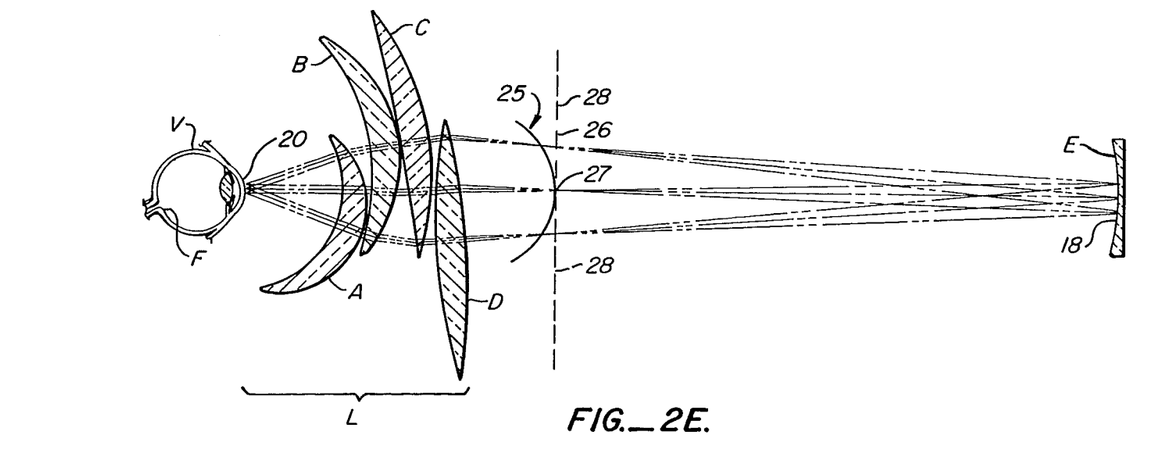
FIG. 2E showing correction of the lens system at a conjugate location of the object (the cornea viewed as an aperture stop) with a mild on axis cylinder lens.

In FIG. 2E, the same lenses are illustrated in section in their final disposition and before more than half of the lens elements are cut away. Thus in FIG. 2E, it is possible to understand the origin of the lens system in terms of whole conventional spherical lenses.

Referring to FIG. 2E, lens A and lens B are respective near-aplanatic concavo-convex lenses disposed towards an object O on the concave side and rotated and displaced to their final disposition. Lens C is a concavo-convex lens that is carried along with the axis of lens B. Lens D is a convexo-convex lens which is rotated about its object conjugate produced by the previous lenses.

Displacement of all lenses occurs so that all "active" rays pass through each lens between an edge and the center. Displacement also occurs so that the center is not used for the overall refraction. Final lens compensation is produced by adding a weak cylinder lens E at or near the focal plane 18 of the system.

Naturally, in the disposition shown in FIG. 2E it would be a waste of over one-half of the optics to use the lenses as illustrated. The lenses are truncated to a shape just containing the active optical area of the lens elements, such as shown in FIG. 1A. Further, it can be seen that less than half of the lens elements are used. This being the case, full lens elements such as those illustrated in FIG. 2E each can contribute to two identical lens systems.

Figure 1B:
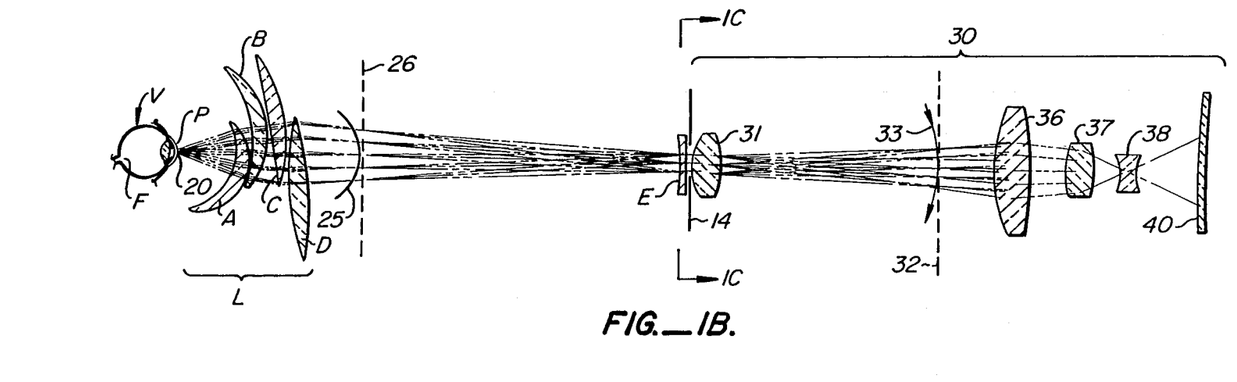
FIG. 1B is a side-elevation section of the lens elements of this invention disposed linearly illustrating a typical application of the lens to a fundus camera schematically shown.

Having shown the non-concentric alignment, displacement, rotation, and use of marginal rays only of the disclosed lens system with respect to FIGS. 2E and 1A, one use of the lens system can be described in the schematic of a fundus camera of FIG. 1B. In understanding the lens system's use as illustrated in FIG. 1B, the function of the lens system in light rejection can be fully understood.

Referring to FIG. 1B, the lens system is generally denominated as L. An eye V has a fundus F and a pupil P. Light passes through the pupil P to form an image of the fundus F through the lens system L.

Those familiar with the anatomy of the eye will realize that the fundus of the eye is approximately spherical. Therefore, there is a natural compensation of the image curvature caused by the lens elements and the natural curvature of the fundus.

Furthermore, in terms of the focus of lens system L, two distinct images will be formed. These are the image of the aperture plate 14 and the image of the light entering and exiting the eye V.

Figure 1C:
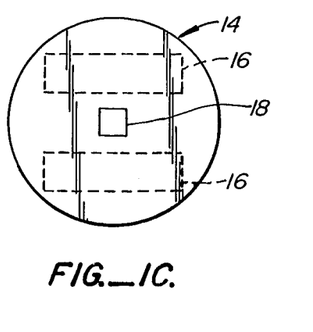
FIG. 1C is an elevation of an aperture plate of a fundus camera along line 1C—1C of FIG. 1B.

Referring to FIG. 1C, a typical aperture plate is shown. It includes first and second light sources 16 and a central aperture 18. Light sources 16 illuminate the fundus of the eye. Aperture 18 receives light back from the fundus of the eye. This aperture passes light to the camera.

The reader will understand that for stereo viewing, two apertures on the order of aperture 18 will be required.

Lens system L will focus an image of the aperture plate 14 onto the convex cornea 20 of the eye. It can be seen that for flare rejection purposes, convex cornea 20 will reject flare from illumination areas 16. Since light will exit the cornea at the focused pupil area 18 (which is not subject to illumination), no flare will come from the passage of the light through the cornea of the eye.

It is important to know that the lens system L must under all circumstances maintain an accurate image of the aperture plate at the cornea 20 of the eye V. Lacking this, flare from the central portion of cornea 20 would undoubtedly be present to degrade the image.

As will hereinafter be more fully explained, minor adjustments to the lens system L to correct aberration do not appreciably change the focus of aperture plate 14. Thus, adjustments to the lens system here described enable an optimum fundus image to be gathered at image plane 40 of camera 30; they do not appreciably affect the focus of the aperture plane 14 to the cornea 20.

In the camera system shown, the fundus images at respective image planes 26, 32, and 40. Each focus plane needs to be understood.

Regarding image plane 26 and referring at the same time to FIG. 2E, the reader will note that eye V with fundus F are illustrated. Fundus F in the back of the eye has a spherical curvature, concave and disposed towards lens system L.

Referring to the rays diverging from the cornea 20, the reader will see as illustrated in both FIGS. 2E and 1B that the light converges along a spherical plane illustrated in section at line 25. This plane is concave and disposed towards eye V.

However, when the lens system L focuses the spherical plane of the fundus F, it will approximately register to the image plane 26 of the fundus. This occurs because conjugates of the fundus corresponding to the peripheral field of the eye will focus slightly further away from focal plane 25, than those conjugates corresponding to the central field of the eye. Thus, the central portion of the fundus will focus on axis at 27 while the peripheral portions of the fundus will be extended beyond plane 25 to plane 26. Image flattening will occur.

Returning solely to FIG. 1B, the rest of the camera system can be easily understood. An objective lens 31 focuses the fundus image F from plane 26 to a second fundus image plane 32. This plane is a convenient place for an aperture in the fundus image plane.

In my copending patent application entitled "Fundus Camera," U.S. Ser. No. 719,779, filed Apr. 4, 1985, I describe a slit scanning system. Utilizing this type of slit scan I have found that the lens system can have slit apertures pass at second fundus plane 32 for photographing the eye. It is important to note that the lens system here illustrated is optimally used with such a slit scan camera as well as other camera configurations, particularly simultaneous stereo imaging cameras. I have shown this slit scan schematically at 33.

It is just as important to note that this device can be used with conventional fundus cameras. For example, a camera with a shutter at plane 32 would work as well. Likewise, shutters could be moved to other locations in the system.

After passing plane 32, light passes through an achromat 36 and then to a camera objective 37 and preferably through color compensator lens 38. Light is focused to form an image of the fundus F at a photoplane 40. It will be understood that photoplane image plane 40 can include camera film, vidicon tube, or any other imaging device.

It is to be noted at this point, that the disclosed lens system is especially suitable for quantitative image enhancement such as digital processing. The reader will observe that in the entire description of the lens system, no stops or image artifacts are located centrally of the image. Such stops or image artifacts make digital processing more complex and less effective because the quantitative processing takes the respective artifact and processes it out of proportion to the rest of the image.

Having set forth an optical train for a fundus camera with which the lens system may be used, the remainder of this specification will consist first of a description of how the lens system is fabricated with reference to FIGS. 2A–2E. Thereafter the specification will discuss the flare rejection property of the lens system briefly with reference to FIGS. 3A, 3H.

Referring to FIGS. 2A–2E, there is illustrated in a cartoon series the construction of the lens systems. Each step is specifically disclosed.

Referring to FIG. 2A, concavo-convex near aplanats A and B are placed concentrically of an axis 50. Concavo-convex spherical lens C and convexo-convex spherical lens D are also placed centrally. The placement therein is imaginary; it could not occur in the real world because of two overlaps 51, 52. These overlaps 51, 52 would destroy the required air/glass interface. As will hereinafter be set forth, once relative rotation of the lens elements occurs, overlap will no longer be present. The required air/glass interface will be restored.

Stopping here the reader will understand that advantage is gained by the overlap. Observing FIG. 2A it will be seen that all rays diverge from a point 55. Assuming that lens elements A and B did not overlap and assuming further that lens elements C and D did not overlap, one can immediately see that both lens element B and lens element D would have to be of greater diameter to capture all the active rays of the optical system.

Further, the distance between lens A and lens D would have to increase. As this distance is increased, the diameter of lens D would likewise also have to increase. Therefore, it will be understood that the compactness of this lens system follows from the design process herein disclosed.

Fortunately, computer programs can emulate air/glass interfaces even though such air/glass interfaces do not in fact exist in the real world. Such an emulation has been undertaken for this design utilizing a Hewlett Packard 9825 Computer and a Hewlett Packard 7225A Plotter, both products of the Hewlett Packard Company of Palo Alto, California. Compatible software obtainable from Sinclair Optics of Fairport, New York, under the product name Oslo-25G was used to emulate the design herein disclosed.

As a starting point in the optical design, the four elements are given powers and shapes such as to minimize the spherical aberration in the imaging of point 55. As a practical matter, this results in low spherical aberration for each element taken separately in regard to producing image conjugates of point 55. Minor changes to the starting values produce optimized performance. Parameters for such an optimized lens system follows.

The preferred optics will now be described. The system includes an aperture stop 1 located 13.407 millimeters (mm) from point 55 (referred to as "surface 0"). The aperture stop is typically 29.7805 mm in diameter and is located 16.701 mm from surface 2 on lens A.

The combined system, as shown in FIG. 2A, has an effective focal length of 38.60 mm in yellow light.

Wavelength traces were generated in yellow (0.58756 micrometers), blue (0.48613 micrometers), and red (0.65627 micrometers).

Regarding glasses used, lenses A and C are glass sold under the designation BK7 by the Schott Company of Duryea, Pennsylvania. Lenses B and D are sold under the product designation LAK8 by the Schott Company of Duryea, Pennsylvania.

Surface 2 on lens A has a curvature of −33.477 mm. Surface 3 on lens A has a sharper curvature of −27.188 mm. Lens A overlaps lens B by 0.704 mm, a computer emulated condition. Lens A is 8.86 mm thick.

Lens B has surface 4 with a curvature of −67.675 mm and surface 5 with a curvature of −43.092 mm. The lens has a thickness of 8.86 mm and is separated by 0.704 mm from lens C.

Lens C has a surface 6 with a curvature of −736.269 mm. Surface 7 has a curvature of −82.664 mm. Overall lens thickness is 8.86 mm. Overlap of surface 7 of lens C into surface 8 of lens D occurs in the amount of 1.759 mm, again a computer emulated condition.

Surface 8 of lens D has a convex curvature of 158.868 mm. Its opposite convex curvature is −238.340 mm. The distance between surface 9 of lens D to the conjugate of point 55 is approximately 224.9 mm. Lens D thickness is 8.86 mm.

Having set forth the parameters of the lens system, the rotation of the elements will now be set forth. First, the rotation will be explained with reference to the series of FIGS. 2B, 2C and 2D. Finally, the rotation will be quantitatively described with respect to FIG. 2E. The reader will understand that the figures here given are for an optimum lens design; those following the teachings herein set forth will understand that individual designers will vary widely in following the broad parameters laid forth herein.

Referring briefly to FIG. 2A, the angle of the lens system therein illustrated is 96°. Because the disclosed system only utilizes half of the lens elements, the angle of the resultant system will be on the order of slightly less than 48°. This is slightly less than 24° on either side of a "principle ray" or average central ray passing down the system.

It will be noted that in reading this application, the designation "principle ray" cannot be understood as such in the traditional sense. Normally, the principal ray passes down the axis of the lens system. In the lens system herein disclosed, there is no axis present!

Lens A has a near aplanatic surface 2. All rays incident upon that surface pass essentially normal to it.

Lens A also deflects rays at surface 3. These deflected rays pass through surface 4 on lens B. Again the rays pass essentially normally with respect to surface 4.

Figure 3A:
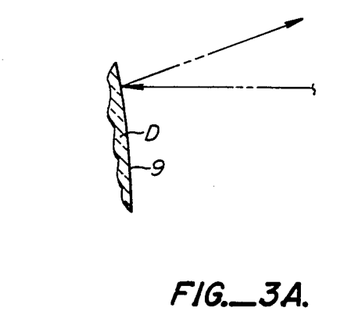
FIGS. 3A–3H are successive cartoon illustrations showing flare rejection of the lens trains actually produced.

Referring to FIG. 2B, lens system A has been displaced and rotated. It has been rotated so that all working rays 57, 59 from point 50 pass between lens center 60 of lens A and lens edge 62 of lens A. As will hereinafter be more apparent with respect to the cartoon series of FIG. 3, this moves the lens center 60 out of the active area of the rays. Moving out of the active areas of the rays, the center cannot be a point of flare emission.

Referring further to FIG. 2B, it will be noticed that lenses B, C, and D have also all been rotated with lens A.

Stopping here, discussion of the relative rotation of the lens elements can be useful.

In my work on this lens design, it will be appreciated that I am using wedge-shaped segments of the peripheries of lenses. It is preferred that the wedges be approximately equal in power and opposite in disposition as they extend across the lens system. This is necessary for the balance of aberrations, dispersions and absorptions encountered through the system.

Referring briefly to FIG. 2E, it can be seen that the upper half of lenses A and D are used. Likewise the lower halves of lenses B and C are used.

I have referred to this type of disposition as down and up or D and U. It will be understood that the embodiment shown in FIG. 2E is preferred and consists of two lens elements (A and D) down, and two lens elements up or DUUD. Likewise, the elements can be alternately up and down, DUDU.

Referring to FIG. 2C, lens element A is shown unchanged with lens elements B, C and D rotated to an upward position. Some attention can be given to the point of lens rotation.

The object point 55 is imaged by lens A to a new position or conjugate which serves as the center of rotation for moving lens B to its new location. (In practice, the image position is best defined by the intersection of a ray passing along the lens axis, and a marginal ray.)

Rotation will occur until the non-prismatic portion of lens B at 70 and the lower edge 72 have the active rays confined therein.

It will be observed that lens elements C and D have been rotated along with element B. Going to FIG. 2D, lens element D only has been rotated. This lens element has been rotated about its conjugate to the object which is 323 mm distant. It will be noted that the rotation, like the rotation of lens elements A, B and C, occurs from a point on the left of FIG. 2D. Again, lens rotation has occurred so that the lens center 80 and lens edge 82 have between them the active rays of the system. Likewise, it is important to note that neutral axis 80 of lens D does not participate in the refraction of the lens system L.

Some small further rotating of the lens elements may be required to reject flare especially in the cases of the lens elements A and B. (See FIGS. 3F and 3H. I find that such rotating can occur preferably about the radius of curvature of one of the lens surfaces and should occur only that amount necessary to reject any flare. For example, a tipping of lens element A about the center of curvature of its surface 3 and a slight tipping of the lens element B about the center of curvature of its surface 5 can occur for optimum flare rejection. Such rotating is in the order of a few degrees and can be either in the plane of FIG. 2D or perpendicular to the plane of FIG. 2D.

At this juncture in the lens design, the parameters can be altered to suit the particular lens design compromise that any application may require. For each such alteration, the designer will want to renew the ray trace and observe tendencies of aberration, distortion, dispersion and the like. For example, slight changes in the lens element refractive properties, tilt and rotation can all occur and be analyzed to minimize or symmetrize resultant spherical aberration, lateral color aberration, curvature of field, nonuniform dispersions, absorptions, and the like. I have found that effectively all aberrations may be balanced and compromised to a satisfactory level, save and except a uniform astigmatic aberration which is of significance at the imaging plane 26 shown in FIG. 2E. By way of example, such aberrations can be held to acceptable levels and be maintained as residual aberrations symmetric about the incoming or outgoing optical axis. It is for this reason that I place a weak cylinder lens E at the focal point of the lens system L as shown in FIG. 2E. Cylinder E is exaggerated in the view of FIG. 2E and in practice is on the order of ⅛th diopter of cylinder power.

Referring to FIG. 2E, the resulting displacement and rotation of the preferred lens system can now be discussed.

Lens system A is rotated by 24° about a point on the axis 50 of the lens. The point is located 30.109 mm to the left of surface 2 illustrated in FIG. 2A.

Lens system B is rotated upwardly from axis 50 by 35.21° about a point 71 on the axis of lens system B located 51.078 mm to the left of surface 4. (See FIG. 2C). Lens C remains in its original position relative to lens B.

Lens D is rotated opposite the remaining lens systems to an angle 6.72° about a point on the axis of lens D located 323.00 mm to the left of surface 8. (See FIG. 2D.)

Thus, the configuration of the preferred lens system is completely set forth.

I have caused the rejection of flare to be individually considered surface by surface in FIGS. 3A-3H.

Figure 3B:
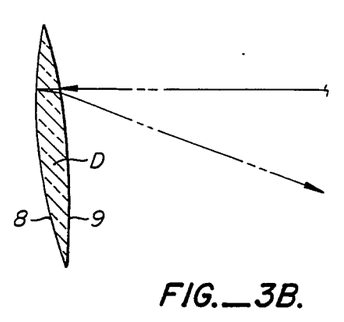
Figure 3C:
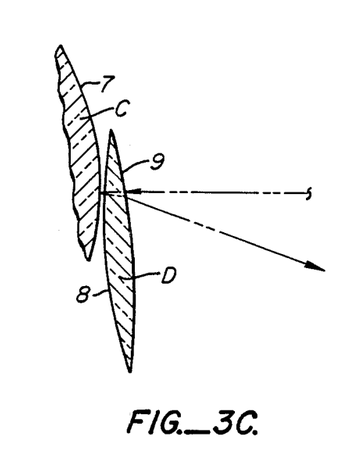
Figure 3D:
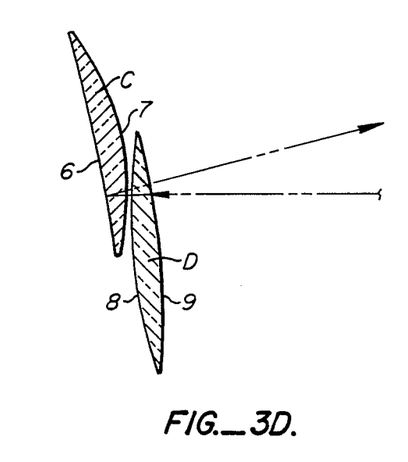
Figure 3E:
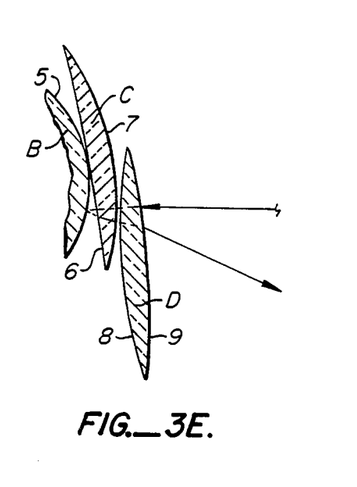
Figure 3F:
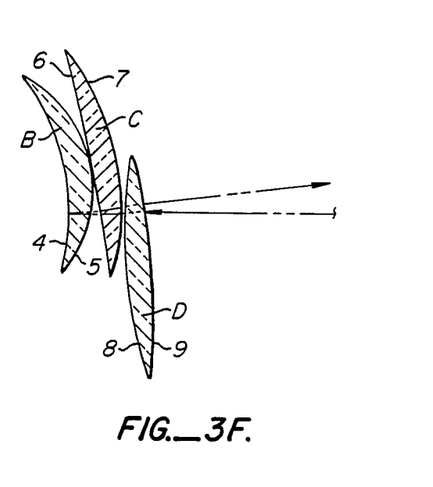
Figure 3G:
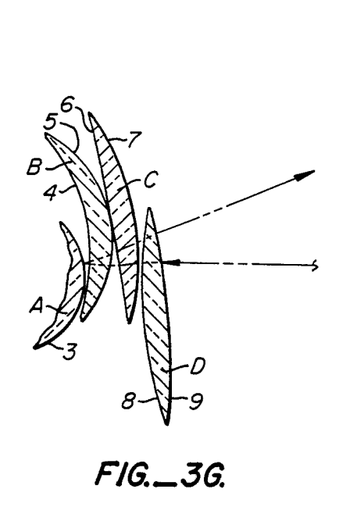
Figure 3H:
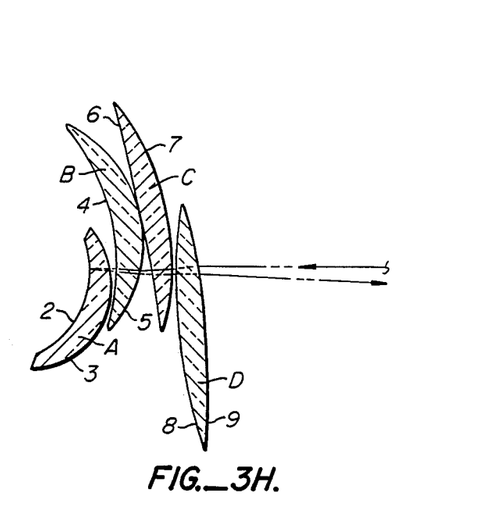

FIGS. 3A and 3B analyze flare with respect to surfaces 9 and 8 on lens D. FIGS. 3C and 3D illustrate flare on surfaces 7 and 6 of lens element C. FIGS. 3E and 3F illustrate flare with respect to surfaces 5 and 4 on lens element B. Finally, FIGS. 3G and 3H illustrate flare with respect to surfaces 3 and 2 on lens element A. It will be noted that these Figures are illustrative of light or flare resulting from rays illuminating the central field of view.

In this application I have used the definition "symmetrical lens element." By this definition I intend to cover any lens element that is symmetrical about an axis of symmetry. Such lenses commonly have the same optical thickness and refractive surface slope at each discrete radius from the axis. Such a definition will include herein both spheric and aspheric surfaces.

The reader should understand that for most beneficial use of the disclosed invention it is required that the optics be coated. Specifically, I have used single layer antireflection coatings of magnesium fluoride on LAK8 glass and a high efficiency optica coating such as HEB-BAR (a trademark of Melles Griot of Irvine, California) on BK7 glass. Such coatings are available from Melles Griot of Irvine, California.

In this lens design, all elements have been optimized to minimize spherical aberration. As a result, lens surfaces (particularly on elements A and B) which look like aplanats have been generated. However, these surfaces are not true aplanatic surfaces. Hence, the term "near aplanatic" has been used.

Figure 4:
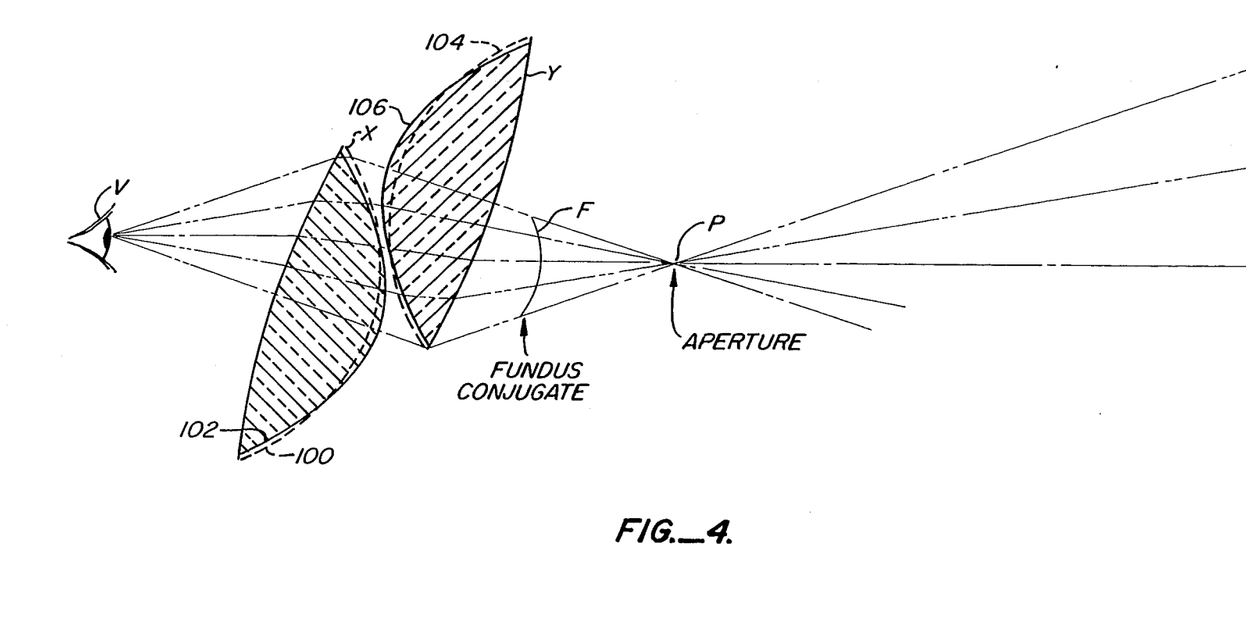
FIG. 4 is an embodiment using two aspheric lens elements.

It has heretofore been emphasized that this invention may be practiced using spherical optics. An alternate embodiment using two aspheric optics only is shown in FIG. 4 utilizing respective aspheric lenses X and Y.

Referring to lens X, a spherical lens surface is shown in broken lines at 100. The aspheric configuration of the lens is shown at 102 and comprises the second refractive interface from the eye E to the pupil P of the optic system. As before an image of the fundus is formed at F.

Likewise, lens Y is similarly described. Specifically, it includes a spherical surface 104 shown in broken lines and the actual aspheric surface 106.

These lenses X and Y each derive their respective aspheric shapes from having the object to image optical path length (i.e. the sum of ray paths multiplied by the index of the medium the ray is traversing) the same for each ray passing through a given lens. While the presence of the aspheric design complicates the production of the discrete lens elements, the reduction in the total number of elements used is believed to justify this embodiment. Furthermore, each aspheric is azimuthally symmetric, simplifying fabrication relative to a more general type of aspheric surface. The aspheric surfaces may be on either or both surfaces of the elements, subject to the aforementioned condition of equal optical path.

In this particular example, the effect of the required rotations results in both lenses being rotated about their respective focal points, these rotations being in opposite directions. Lens X has been rotated downwardly relative to an object point adjacent eye V to cause only the top half of the lens element to be used. Likewise, lens Y has been rotated upwardly about pupil P to cause the lower half of the lens element to be utilized.

Although aspheric surfaces must be constructed in this embodiment, for each pair of aspheric lenses utilized, two discrete lens systems can be constructed. This is because the lower portions of the lens and the upper portions of the lens not used in one lens construction can be used in a second lens construction.

Dimensioning of the aspheric lenses can proceed as previously described using conventional ray tracing programs.

Optimally, I prefer a rotation of the lenses each in the range of 17.5°.

From the two specific embodiments here illustrated, it will be seen that the flare rejection lens assembly of my invention will be seen to admit of numerous embodiments.

I claim:

1. A flare rejection refracting lens train having two aspherical sequential lens elements wherein each lens element includes at least one surface having an aspheric shape to impart to the lens the object to image optical path length the same for each passing ray, each lens element further including a segment of less than one-half of a symmetrical lens element.

2. The flare rejection lens train of claim 1 and wherein at least two of the lens elements are rotated one with respect another.

3. A flare rejection lens train having at least three spherical elements, said lens elements when aligned concentrically forming a lens train having minimal spherical aberration, said lens elements displaced and rotated so that refracted rays through the lens system use lens portions between the center and edge of one-half of the lens and do not use the central portion of the lens and the other half of the lens.

4. The flare rejection lens train of claim 3 and wherein each element as displaced has a corresponding lens element oppositely displaced.

5. The flare rejection lens train of claim 3 and wherein said lens elements are displaced and rotated by rotation substantially about a set of focal conjugates of the lens system.

6. The flare rejection lens train of claim 3 and wherein at least one of the spherical lenses is an aplanat.

7. The flare rejection lens train of claim 6 and including at least two aplanats.

8. A camera having a wide angle lens system for photographing an object including a film plane, a shutter system and a wide angle objective lens system, said wide angle objective lens system including the flare rejection lens train of claim 3.

9. A camera according to claim 8 and wherein said wide angle lens system includes at least four spherical lens elements including first and second spherical lenses having near aplanatic surfaces followed by two spherical lenses;

the first and last of said lenses displaced in one direction to use lens portions between the lens center and one edge;

the intermediate lens elements displaced in an opposite direction to use lens portions between the other lens edge and center.

10. The invention according to claim 9 and wherein shutter mechanism of said camera includes a scanning slit.

11. A camera according to claim 8 and wherein said wide angle lens system includes at least four spherical lens elements including first and second spherical lenses having near aplanatic surfaces followed by two spherical lenses;

the first and third of said lenses displaced in one direction to use the lens portions between the lens center and one edge;

the second and fourth lens elements displaced in an opposite direction to use the lens portions between the other lens edge and center.

12. A wide angle lens system comprising in combination:

at least two concavo-convex spherical lenses, each having a near aplanatic surface, the near aplanatic surface of the first lens substantially normal to rays from a first point and spherically deflecting rays to apparent emanation from a second point;

the near aplanatic surface of the second lens substantially normal to rays apparently emanating from the second point;

said first and second lenses equally and oppositely displaced so that all rays refracted by the lens system pass between the lens center of each lens and one-half of the lens without passing through the other half of the lens.

13. The wide angle lens system of claim 7 and including a third spherical lens.

14. The wide angle lens system of claim 13 and wherein said third lens is displaced so that all rays refracted by the lens system pass between the neutral lens center of each lens and one-half of the lens without passing through the lens center and the other half of the lens.

15. A wide angle flare rejection lens system including four sequentially, equally-powered spherical component lenses, these lenses comprising at least two, paired concavo-convex lenses each having a near aplanatic surface, and at least two spherical lenses each having at least one convex surface;

first and last lenses in said sequential lens train displaced in a first direction to use lens portions between the lens center and one edge;

the intermediate lenses displaced in an opposite direction to use lens portions between the other lens edge and center;

none of the lens elements using the neutral central portion.

16. A camera having a wide angle lens system for photographing an object including a film plane, a shutter system, and a wide angle objective lens system, wherein the wide angle objective lens system includes the flare rejection refracting lens train of claim 1.

* * * * *